United States Patent
Oldfield et al.

(10) Patent No.: US 9,486,542 B2
(45) Date of Patent: Nov. 8, 2016

(54) COMPOSITIONS AND METHODS FOR IN VIVO EVALUATION OF BIOLUMINESCENCE

(71) Applicant: Caliper Life Sciences, Alameda, CA (US)

(72) Inventors: Stephen Oldfield, Alameda, CA (US); Daniel Ansaldi, Alameda, CA (US); Rajendra Singh, San Jose, CA (US); Ning Zhang, Alameda, CA (US)

(73) Assignee: Caliper Life Sciences, Alameda, CA (US)

( * ) Notice: Subject to any disclaimer, the term of this patent is extended or adjusted under 35 U.S.C. 154(b) by 0 days.

(21) Appl. No.: 14/606,817

(22) Filed: Jan. 27, 2015

(65) Prior Publication Data

US 2015/0143554 A1    May 21, 2015

Related U.S. Application Data

(63) Continuation of application No. 12/807,895, filed on Sep. 16, 2010, now abandoned.

(60) Provisional application No. 61/276,989, filed on Sep. 18, 2009.

(51) Int. Cl.
| | |
|---|---|
| *A61K 48/00* | (2006.01) |
| *A61K 49/00* | (2006.01) |
| *G01N 21/76* | (2006.01) |
| *G01N 33/58* | (2006.01) |
| *A01K 67/027* | (2006.01) |
| *G01N 21/27* | (2006.01) |

(52) U.S. Cl.
CPC ....... *A61K 49/0021* (2013.01); *A01K 67/0275* (2013.01); *A61K 49/0013* (2013.01); *A61K 49/0017* (2013.01); *G01N 21/763* (2013.01); *G01N 33/582* (2013.01); *A01K 2267/03* (2013.01); *G01N 21/274* (2013.01)

(58) Field of Classification Search
CPC .................... A61K 49/0021; A61K 49/0017; A61K 67/0275
See application file for complete search history.

(56) References Cited

U.S. PATENT DOCUMENTS

| | | | |
|---|---|---|---|
| 4,665,022 A | 5/1987 | Schaeffer et al. | |
| 4,764,235 A | 8/1988 | Hazama et al. | |
| 5,374,534 A | 12/1994 | Zomer et al. | |
| 5,377,676 A | 1/1995 | Vari et al. | |
| 5,650,135 A | 7/1997 | Contag et al. | |
| 6,217,847 B1 | 4/2001 | Contag et al. | |
| 6,649,143 B1 | 11/2003 | Contag et al. | |
| 6,703,220 B1 * | 3/2004 | German | C07K 14/47 435/252.3 |
| 6,908,605 B2 | 6/2005 | Contag et al. | |
| 6,916,462 B2 | 7/2005 | Contag et al. | |
| 6,923,951 B2 | 8/2005 | Contag et al. | |
| 6,939,533 B2 | 9/2005 | Contag et al. | |
| 7,198,774 B2 | 4/2007 | Contag et al. | |
| 7,255,851 B2 | 8/2007 | Contag et al. | |
| 7,449,567 B2 | 11/2008 | Zhang et al. | |
| 7,449,615 B2 | 11/2008 | Contag et al. | |
| 2004/0166553 A1 | 8/2004 | Nguyen et al. | |
| 2005/0164321 A1 * | 7/2005 | Riss | C12Q 1/66 435/8 |
| 2007/0131924 A1 * | 6/2007 | Pyun | G01N 21/76 257/32 |
| 2008/0293795 A1 | 11/2008 | Donawho et al. | |
| 2009/0047219 A1 | 2/2009 | Ohmiya et al. | |
| 2009/0060843 A1 | 3/2009 | Berggren et al. | |

FOREIGN PATENT DOCUMENTS

EP    1 865 073 A1    12/2007

OTHER PUBLICATIONS

Information sheet from Wright Cell Imaging Facility. Autofluorescence: Causes and Cures. Printed from http://www.uhnres.utoronto.ca/facilities/wcif/fdownload2.html, website dated Nov. 2006. pp. 1-8.*
Takakura et al. Chem Asian J. 2011.*
Wang et al. Mol Genet Genomics 268:160-168, 2002.*
Honigman et al. Molecular Therapy 4(3):239-249, 2001.*
Shaner et al. Nature Methods. 2(12):905-909, 2005.*
Choy et al. BioTechniques 35:1022-1030, 2003.*
Berger, et al., "Uptake Kinetics and Biodistribution of 14C-D-Luciferin—A Radiolabeled Substrate for the Firefly Luciferase Catalyzed Bioluminescence Reaction: Impact on Bioluminescence Based Reporter Gene Imaging," *Eur. J. Nuclear Medicine and Mol. Imaging* 35:2275-2285 (2008).
Collaco, et al., "Monitoring Immediate—Early Gene Expression Through Firefly Luciferase Imaging of HRS/J Hairless Mice," *BMC Physiology* 3(1):8 (pp. 1-11).
Kajiyama & Nakano, "Isolation and Characterization of Mutants of Firefly Luciferase Which Produce Different Colors of Light," *Protein Engineering* 4:691-693 (1991).
Lee, et al. "Cell Uptake and Tissue Distribution of Radioiodine Labeled D-Luciferin: Implications for Luciferase Based Gene Imaging," *Nuclear Medicine Communications* 24:1003-1009 (2003).
Mocanu, et al., "Combined In Vivo Bioluminescence and Fluorescence Imaging for Cancer Gene Therapy," *Molecular Imaging* 3(4):352-355 (2004).
Reynolds, et al., "Imaging of Spontaneous Canine Mammary Tumors Using Fluorescent Contrast Agents," *Photochemistry and Photobiology* 70:87-94 (1999).
Theodossiou, et al., "Firefly Luciferin-Activated Rose Bengal: In Vitro Photodynamic Therapy by Intracellular Chemiluminescene in Transgenic NIH 3T3 Cells," *Cancer Research* 63:1818-1821 (2003).
Weissleder, et al., "Shedding Light Onto Live Molecular Targets," *Nature Medicine* 9:123-128 (2003).

* cited by examiner

*Primary Examiner* — Marcia S Noble
(74) *Attorney, Agent, or Firm* — Pasternak Patent Law

(57) ABSTRACT

Compositions and methods are described for normalizing a bioluminescent signal in a live animal.

11 Claims, 4 Drawing Sheets
(4 of 4 Drawing Sheet(s) Filed in Color)

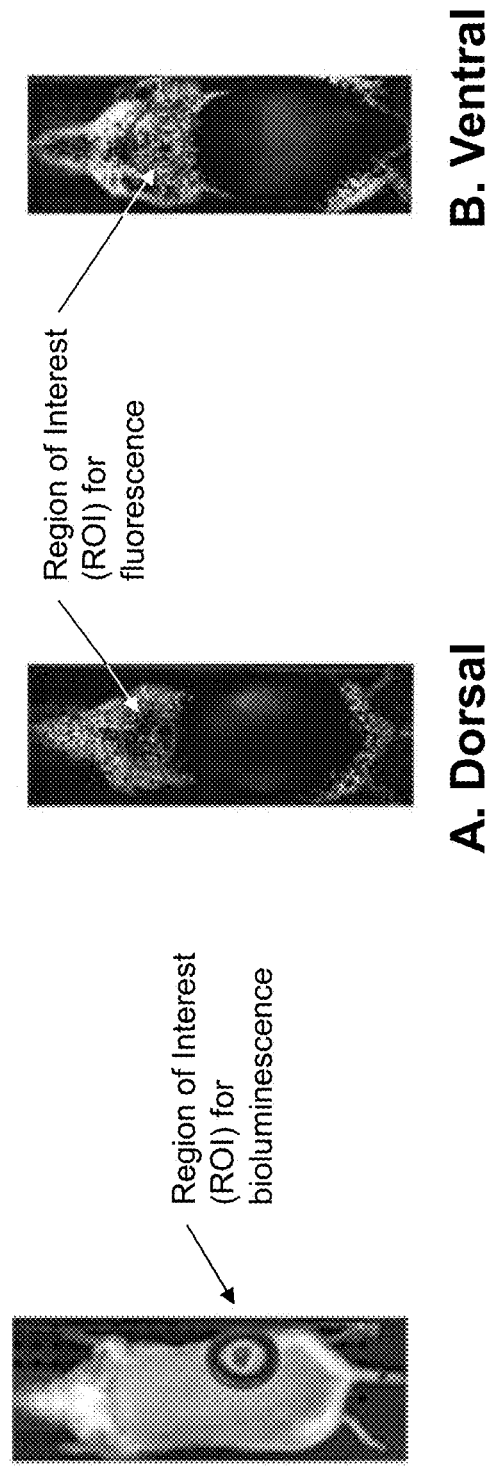

COMPOSITIONS AND METHODS FOR IN VIVO EVALUATION OF BIOLUMINESCENCE

CROSS-REFERENCE TO RELATED APPLICATIONS

The present application is a continuation of U.S. patent application Ser. No. 12/807,895, filed Sep. 16, 2010, which claims the benefit of U.S. Provisional Application No. 61/276,989, filed Sep. 18, 2009. The disclosure of which is hereby incorporated by reference in its entirety.

TECHNICAL FIELD

The present disclosure is in the field of reagents for use in evaluation of bioluminescence in a living organism. In particular, described herein are compositions and methods for normalizing the bioluminescent signal observed from an organism containing a bioluminescent protein using a fluorescent dye.

BACKGROUND

Detection of light from transgenic animals carrying a gene encoding a light-generating protein is a powerful tool in diagnostics, drug discovery and medicine that allows for the identification of disease pathways, determination of mechanisms of action, evaluation of efficacy of drug compounds, and monitoring lead candidates' effects on disease progression in living animals. See, e.g., U.S. Pat. Nos. 7,449,615; 7,255,851; 7,198,774; 6,939,533; 6,923,951; 6,916,462; 6,908,605; 6,890,515; 6,649,143; 6,217,847; and 5,650,135.

In the case of bioluminescent proteins a substrate is typically administered to the animal prior to the evaluation. For example, luciferase (e.g., encoded by eukaryotic luc gene), catalyses the oxidation of D-luciferin (D-(−)-2-(6'-hydroxy-2'benzothioazolyl)thiazoline-4-carboxylic acid) in the presence of ATP to generate light signals. The availability of the substrate has been shown to effect photon emission efficiency. See, e.g., Lee et al. (2003) *Nuclear Medicine Communications* 24:1003-1009; Berger et al. (2008) *Eur. J. Nuclear Medicine and Mol. Imaging* 35(12):2275-2285. Various derivatives of luciferin have been prepared, including preparations in which luciferin is covalently bonded to a targeting moiety (see, e.g., U.S. Pat. No. 4,665,022) or a fluorescent label (see, e.g., 5-fluoroluciferin available from Promega) as well as 6-substituted D-luciferin esters for use evaluation of pesticides (see, e.g., U.S. Pat. No. 5,374,534).

Despite the wide-spread use of bioluminescent imaging techniques, there remains a need a need for improved methods for detecting, quantifying and validating bioluminescence in living animals.

SUMMARY

The present invention includes compositions and methods for evaluating and quantifying bioluminescence in a living animal by providing a tracking dye that co-distributes with the bioluminescent substrate administered to the animal.

Thus, in one aspect, described herein is a composition comprising a bioluminescent substrate and a tracking dye. In certain embodiments, the bioluminescent substrate comprises luciferin and the tracking dye comprises a fluorescent dye.

In another aspect, described herein is a method of normalizing a bioluminescent signal detected in a live animal comprising a bioluminescent protein by administering a composition comprising a bioluminescent substrate (e.g., luciferin) and a tracking dye (e.g., a fluorescent tracking dye) as described herein to the animal, measuring the bioluminescent signal generated by reaction of the bioluminescent substrate and protein, measuring the signal of the tracking dye (e.g., fluorescence) and normalizing the bioluminescent signal to the signal of the tracking dye. The normalizing may involve finding an average fluorescence signal and determining the deviation of the fluorescence signal in an individual animal from the average fluorescence signal. If the deviation is greater than a set amount (e.g., 30% more or less than the average), the animal is re-imaged. In certain embodiments, the normalizing is done using one or more of Equations (1), (2) and (3), shown below. In certain embodiments, normalizing is done by a computer program (e.g., software).

In yet another aspect, described herein is a method of validating bloodstream injection of a bioluminescent substrate (e.g., luciferin) into a living animal by administering a composition comprising a bioluminescent substrate (e.g., luciferin) and a tracking dye (e.g., a fluorescent tracking dye) as described herein to the animal, localizing the signal emitted by the tracking dye, wherein if the tracking dye signal is localized at the site of injection, the bioluminescent substrate was not distributed via the bloodstream.

In yet another aspect, provided herein are kits comprising any of the compositions as described herein for carrying out any of the methods described herein. In certain embodiments, the kits comprise, in separate or the same containers, a bioluminescent substrate and a tracking dye. The kits may also comprise instructions regarding reconstitution of reagents, injection of reagents into live animals and/or imaging, normalization and validation protocols.

These and other embodiments will readily occur to those of skill in the art in view of the disclosure herein.

BRIEF DESCRIPTION OF THE FIGURES

The file of this patent contains at least one drawing executed in color. Copies of this patent with color drawings will be provided by the Patent and Trademark Office upon request and payment of the necessary fee.

FIG. 1 is an overview of bioluminescence in a mouse injected with a luciferin/fluorescent dye formulation. The region of interest (ROI) for bioluminescence is marked by a circle.

FIG. 2, panels A and B, depict dorsal (FIG. 2A) and ventral (FIG. 2B) views of fluorescence in mice injected with a luciferin/dye formulation. The region of interest (ROI) for fluorescence is marked by a circle.

DETAILED DESCRIPTION

Figure 3:
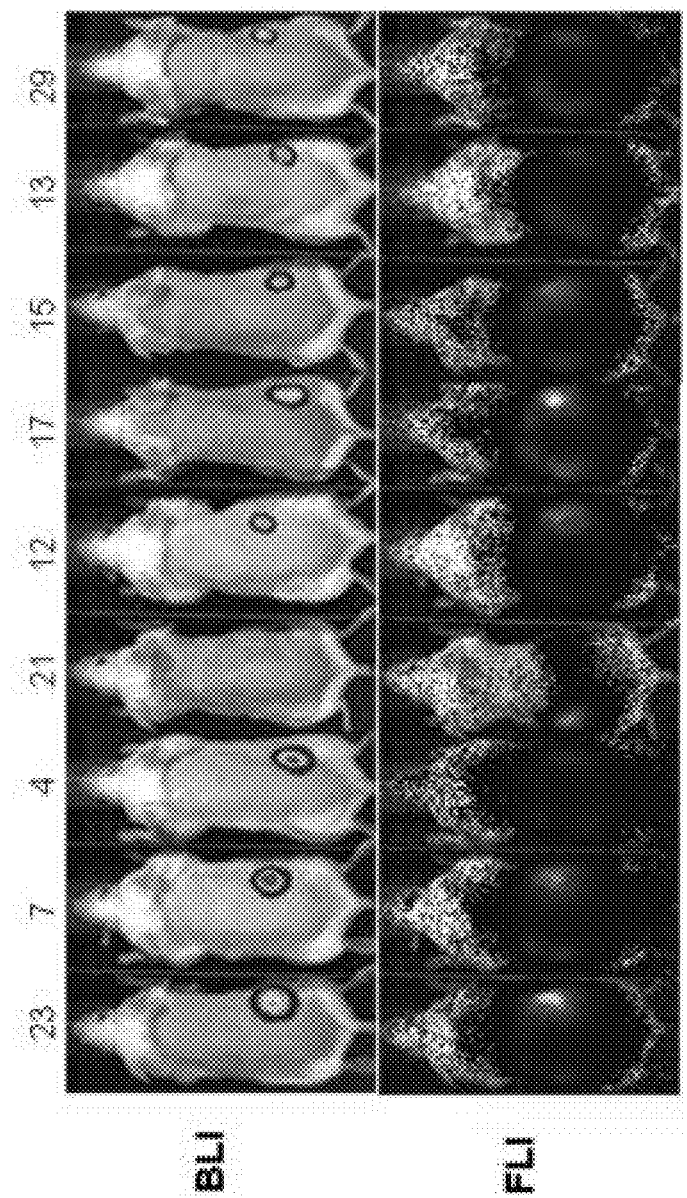
FIG. 3 shows bioluminescence (top panels, labeled BLI) and fluorescent (bottom panels, labeled FLI) in animals injected with a luciferin/dye formulation. The number of the animal is indicated above the panels.

The practice of the present invention will employ, unless otherwise indicated, conventional methods of chemistry, biochemistry, and recombinant DNA techniques, within the skill of the art. Such techniques are explained fully in the literature. See, e.g., A. L. Lehninger, *Biochemistry* (Worth Publishers, Inc., current addition); Sambrook, et al., *Molecular Cloning: A Laboratory Manual* (2nd Edition, 1989); *Short Protocols in Molecular Biology*, 4th ed. (Ausubel et al. eds., 1999, John Wiley & Sons); *Molecular Biology Techniques: An Intensive Laboratory Course*, (Ream et al., eds., 1998, Academic Press); *PCR (Introduction to Biotechniques Series)*, 2nd ed. (Newton & Graham eds., 1997, Springer Verlag); and *Methods In Enzymology* (S. Colowick and N. Kaplan eds., Academic Press, Inc.).

All publications, patents and patent applications cited herein, whether supra or infra, are hereby incorporated by reference in their entireties.

1. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a nucleic acid" includes a mixture of two or more such nucleic acids, and the like.

As used herein, "luminescence" refers to the detectable electromagnetic (EM) radiation, generally, UV, IR or visible light that is produced when the excited product of an exergic chemical process reverts to its ground state with the emission of light. Chemiluminescence is luminescence that results from a chemical reaction. Bioluminescence is chemiluminescence that results from a chemical reaction using biological molecules (or synthetic versions or analogs thereof) as substrates and/or enzymes. Thus, "bioluminescence" refers to the emission of light by biological molecules, particularly proteins. The essential condition for bioluminescence is molecular oxygen, either bound or free in the presence of an oxygenase, a luciferase and ATP, which acts on a substrate, a luciferin. Bioluminescence is generated by an enzyme or other protein (e.g., luciferase) that is an oxygenase that acts on a substrate (e.g., luciferin) and transforms the substrate to an excited state, which upon return to a lower energy level releases the energy in the form of light. Substrates and enzymes for producing bioluminescence, include, for example, luciferin and luciferase, respectively. The luciferin and luciferases may be from any species.

"Luciferase," unless stated otherwise, includes prokaryotic and eukaryotic luciferases, as well as variants possessing varied or altered optical properties, such as luciferases that produce different colors of light (e.g., Kajiyama & Nakano (1991) *Protein Engineering* 4(6):691 693).

"Luciferin" refers to the substrate for luciferase. Luciferin is a low molecular weight organic compound that consists of a benzothiazole moiety attached to a thiazole carboxylic acid moiety. Luciferin is found in fireflies and other animals which, in the presence of ATP and the enzyme luciferase, becomes luminescent. Luciferin is able to pass the blood brain barrier, the blood placenta barrier and the blood testis barrier to distribute quickly through the animal and, toxicity appears low. Luciferin distributes quickly and easily throughout the animal. Luciferin does not affect the animals deleteriously (no evidence of toxicological or immunological effects).

"Light-generating" is defined as capable of generating light through a chemical reaction or through the absorption of radiation.

A "light generating protein" or "light-emitting protein" is a protein capable of generating light. Typically, the light is in the visible spectrum (between approximately 350 nm and 800 nm). Examples include bioluminescent proteins such as luciferases, e.g., bacterial and firefly luciferases.

"Animal" as used herein typically refers to a non-human mammal, including, without limitation, farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

A "transgenic animal" refers to a genetically engineered animal or offspring of genetically engineered animals. A transgenic animal usually contains material from at least one unrelated organism, such as from a virus, plant, or other animal. The "non-human animals" of the invention include vertebrates such as rodents, non-human primates, sheep, dogs, cows, amphibians, birds, fish, insects, reptiles, etc. The term "chimeric animal" is used to refer to animals in which the heterologous gene is found, or in which the heterologous gene is expressed in some but not all cells of the animal.

As used herein, the term "tracking dye" refers to any molecule that, when injected with the bioluminescent substrate, distributes throughout the animal in the same or similar manner as the bioluminescent substrate. Non-limiting examples of "tracking dyes" include, but not limited to, radioactive isotopes, fluorescent molecules, chemiluminescers, chromophores, enzymes, enzyme substrates, enzyme cofactors, enzyme inhibitors, semiconductor nanoparticles, dyes, metal ions, metal sols, and the like. The term "fluorescer" refers to a substance or a portion thereof which is capable of exhibiting fluorescence in the detectable range.

2. General

Before describing the compositions and methods in detail, it is to be understood that the disclosure is not limited to particular formulations or process parameters as such may, of course, vary. It is also to be understood that the terminology used herein is for the purpose of describing particular embodiments only, and is not intended to be limiting.

Although a number of methods and materials similar or equivalent to those described herein can be used, exemplary preferred materials and methods are described herein.

The present disclosure relates to compositions (e.g., reagents) comprising a bioluminescent substrate and one or more tracking dyes. These reagents are formulated for injection into a live animal such that the tracking dye(s) and substrate are similarly distributed in the animal. Thus, the signal from the tracking dye(s) can be measured in tissues that provide a luminescent signal and the signal from the tracking dye used to audit and normalize the bioluminescent signal resulting from the reaction of substrate in the reagent and luciferase in the animal. Normalizing the tracking dye signal to the bioluminescent signal allows for greater statistical validity of the bioluminescent measurements.

In addition, the compositions and methods described herein can be used to validate injection of the bioluminescent substrate into the desired target within the organism. For example, if the bioluminescent substrate is intended to be injected into the abdominal cavity so as to be distributed over the animal via the bloodstream, but is mistakenly injected into the intestine, the presence of the tracking dye will allow the researcher to confirm that the substrate is not trapped in an undesired location of the animal.

Reagents

The compositions (reagents) described herein include both a substrate for a bioluminescent protein and a tracking dye.

Bioluminescent substrates and formulations comprising these substrates are well known in the art and are commercially available. In certain embodiments, the bioluminescent substrate of the invention comprises luciferin (e.g., D-luciferin). For the reagents described herein, the luciferin is typically provided as a potassium salt of defined weight. Liquid reagents may also be used. In preferred embodiments, fresh stocks of luciferin-containing reagents are prepared in the appropriate buffer (e.g., DPBS) just prior to imaging of the animal and the stocks filter sterilized, for example through a 0.2 µM filter.

Dry luciferin can be reconstituted at the desired concentration, typically from 10 to 50 mg/ml. In certain embodiments, the luciferin is reconstituted such that the stock reagent is at 30 mg/ml. Dosages can be readily determined by the skilled artisan. Generally, for administration, luciferin is administered at a dose of approximately 150 mg/kg. Thus, for a 30 g animal, 150 µl of a 30 mg/ml luciferin solution should be administered for delivery of 4.5 mg of luciferin to the animal.

Luciferin-containing reagents can be administered to live animals by any suitable method, including but not limited to, by intravenous, subcutaneous, intraperitoneal, mucosal routes and the like. Typically, in live animals, luciferin is administered intraperitoneally, optionally with anesthesia. Luciferin kinetic studies can be performed following the instructions provided by the manufacturer (e.g., Caliper Life Sciences).

As noted above, the compositions described herein also comprise a tracking dye. Any tracking dye that is non-toxic and distributes within the animal with the bioluminescent substrate (e.g., luciferin) can be used. In certain embodiments, the tracking dye is a fluorophore. Fluorescent dyes are well known in the art, and include, but are not limited to 6-FAM (Fluorescein) (emits green), Cy 3 (emits red), Cy 3.5 (emits purple), Cy 5 (emits violet), Cy 5.5 (emits blue), Cy 7 (emits near IR), IndoCyanine Green, DyLight 350 (emits violet), DyLight 405 (emits violet), DyLight 488 (emits green), DyLight 549 (emits yellow), DyLight 594 (emits orange), DyLight 633 (emits red), DyLight 649 (emits red), DyLight 680 (emits far-red), DyLight 750 (emits near-IR), DyLight 800 (emits near-IR) Alexa Fluor 488 (emits cyan-green), Alexa Fluor 568 (emits orange), Alexa Fluor 750 (emits red), CF 488 (emits green), CF 555 (emits orange), CF 750 (emits red). The excitation maximums and emission maximums of the selected fluorescent dyes are well known and it will be apparent that the tracking dye is selected to emit at a different wavelength than the bioluminescent protein so as to differentiate between the bioluminescent signal and the signal from the tracking dye.

The tracking dye can be added to the luciferin-containing solution prior to or after the luciferin. Thus, the tracking dye can be added following reconstitution of luciferin in the appropriate buffer.

It will be apparent that the concentration of tracking dye included in the compositions as described herein will vary according to the selected dye in a range.

Imaging

Animals treated with the luciferin and tracking dye compositions as described herein are imaged as described in U.S. Pat. Nos. 5,650,135 and 7,449,567 and as described in the materials provided by the manufacturer of the IVIS™ imaging systems, Caliper Life Sciences.

In vivo imaging can be performed using the naked eye or any sort for camera (still or video). In certain embodiments, an intensified CCD camera sensitive enough to detect the bioluminescent signal and with wide enough dynamic range to also detect the fluorescent signal is used for imaging. Suitable cameras are known in the art and include, but are not limited to, an integrated imaging system (IVIS™ Imaging System, Caliper Life Sciences) controlled using LivingImage™ software (Caliper Life Sciences).

The reagent containing the bioluminescent substrate (e.g., luciferin) and tracking dye is typically injected into the intraperitoneal cavity at a luciferin dose of 150 mg/kg body weight (30 mg/ml Luciferin stock) between about 1 minute and 1 hour prior to imaging, preferably between 1 and 10 minutes, including about 1, 2, 3, 4, 5, 6, 7, 8 or 9 minutes prior to imaging. Mice are typically anesthetized (e.g., Nembutal (25-50 mg/kg body weight) or in a gas chamber with an isoflurane/oxygen mixture and isoflurane tubing placed on the animals' noses), and placed on the imaging stage under anesthesia. Animals are typically imaged for between about 1 and 5 minutes on one or more sides for bioluminescence and from 0.5 to 5 seconds for fluorescence. When imaging for fluorescence signal an excitation of 745 nm and an emission of 800 nm can be used depending on the dye selected. Both bioluminescence (photon emission) and fluorescence can be quantified using LivingImage™ software (Caliper Life Sciences).

Methods

The compositions described herein allow for the normalization of bioluminescent signals and for the real-time validation of proper distribution of the bioluminescent substrate.

In order to normalize values, the bioluminescent signal from the region of interest is measured according to standard protocols previously described. For the fluorescence measurement a region of interest is selected remote from the site of injection in order to determine the systemic distribution of the dye and substrate. The region of interest is quantified according to standard protocols and recorded in efficiency units.

The fluorescent signal from an individual animal can be compared to the average signal measured for a cohort of animals at a particular time point, or the average for a single animal measured at different time points over a longitudinal study.

A fluorescent signal that deviates more than a pre-determined percentage (e.g., between more than 10%, more preferably between about 20%, and even more preferably more than 30%) from the average signal indicates an aberrant substrate injection and the associated bioluminescent measurement should be discarded or repeated. A fluorescent signal that deviates a lesser percentage from the average can indicate injection variability and the percentage deviation used to correct the bioluminescent signal. Normalizing calculations may be performed by a computer or by hand.

Furthermore, the compositions described herein also allow for the validation of distribution of the bioluminescent substrate within the subject animal. In particular, if it is intended that the bioluminescent substrate be distributed via the bloodstream (e.g., by IP injection in the abdomen), the ability to monitor the location of the fluorophore can provide real-time information on injections, for example if the bioluminescent substrate is localized within a body region or part (e.g., intestines).

Kits

The present invention also provides kits comprising the reagents described herein and for carrying out the methods described herein. In particular, these kits typically include a pre-made luciferin/tracking dye reagent or individual elements of luciferin and tracking dye. The kit optionally includes buffers and containers as well as written instructions for carrying out the methods described herein. In the case of prepackaged reagents, the kits optionally include pre-measured or pre-dosed reagents that are ready to incorporate into the methods without measurement, e.g., pre-measured fluid aliquots, or pre-weighed or pre-measured solid reagents that may be easily reconstituted by the end-user of the kit.

3. Experimental

Below are examples of specific embodiments for carrying out the present disclosure. The examples are offered for illustrative purposes only, and are not intended to limit the scope of the present disclosure in any way.

Example 1

Preparation of Bioluminescent/Fluorescent Composition and Imaging

Luciferin/dye formulation was prepared as follows. Ten mL of DPBS to 10 mg of DL800 to dissolve the dye, and aliquoted into 1 mL stock (DL800 stock). Ninety-nine mL of DPBS was added to 3 grams of D-Luciferin, Firefly, potassium salt. One mL of DL800 stock was added to 99 mL of D-Luciferin to formulate the final Luciferin/dye with fluorescence dye concentration of 9.7 ug/mL and D-Luciferin concentration of 30 mg/mL.

Mice containing orthotopic tumors were injected intraperitoneal (i.p.) with 150λ, of Luciferin/fluorescent dye working solution. Six minutes post-injection the mice were placed in a clear Plexiglas anesthesia box (2.5-3.5% isofluorane) of an IVIS™ imaging systems (Caliper Life Sciences) that allows unimpeded visual monitoring of the animals (e.g. visual determination of breathing). The tube that supplies the anesthesia to the box was plumbed to the anesthesia manifold located inside the imaging chamber. After the mice were fully anesthetized, they were transferred from the box to the nose cones attached to the manifold in the imaging chamber, the door was closed, and the "Acquire" button (part of Living Image® program) on the computer screen was activated.

For bioluminescence imaging, the imaging time was up to five minutes per side (dorsal/ventral), depending on the experiment. When the mice were turned from dorsal to ventral (or vice versa), they could be visibly observed for any changes in vitality. Bioluminescence imaging utilized the Block and Open filters inside the imaging chamber.

For fluorescence imaging, the imaging time was from 0.5 to 5 seconds per side (dorsal/ventral), depending on the experiment. When imaging for fluorescence signal an excitation of 745 nm and an emission of 800 nm was used. This filter pair was selected using the Living Image® program.

Bioluminescent and fluorescent signals were quantified using the Living Image® program as follows. For bioluminescence, a region of interest (ROI) is drawn around the area expressing luminescent signal (FIG. 1). This signal is recorded as photons/second. For quantification of fluorescence, the region of interest was placed away from the abdominal region where the substrate was i.p. injected in order to get a better read out of the systemic distribution of the substrate (see, FIGS. 2A and 2B). For dorsal images, the ROI was drawn around the scruff area (back of neck) for quantification of the reference fluorescence signal (FIG. 2A), while for ventral images the ROI was drawn around the thoracic region (FIG. 2B). Fluorescent signal was recorded in efficiency units.

Results of imaging are shown in Table 1 and FIG. 3. In FIG. 3, the top panels show bioluminescence and the bottom panels show fluorescence. The animal number is provided above each set of panels.

TABLE 1

|    | Bioluminescence | Fluorescence |
|----|-----------------|--------------|
| 23 | 7.56E+08        | 2.56E−06     |
| 7  | 9.07E+08        | 2.97E−06     |
| 4  | 5.73E+08        | 3.12E−06     |
| 21 | 8.69E+05        | 1.41E−06     |
| 12 | 2.24E+08        | 2.17E−06     |
| 17 | 4.53E+08        | 2.70E−06     |
| 15 | 2.19E+08        | 2.19E−06     |
| 13 | 2.28E+08        | 1.96E−06     |
| 29 | 2.20E+08        | 2.31E−06     |

As can be seen, mouse 21 did not provide a strong bioluminescent or fluorescent signal, indicative of a poor injection.

Example 2

Normalization of Bioluminescent Signal

The luciferin/dye formulations described herein have the advantage of utilizing Fluorescent signal to normalize the bioluminescent signal. As described in Example 1 and shown in FIG. 3, bioluminescent imaging showed an animal (mouse 21) that had a poor injection, as shown by the absence of luminescent signal, and this was confirmed when looking at the corresponding fluorescent images, showing mouse 21 with a lower level of dye distribution as compared with the other mice.

The average fluorescent signal obtained in Example 1 was obtained, with outliers (mouse 21) omitted. Without mouse 21, the average fluorescence signal was calculated to be 2.50E-06. The fluorescent signal obtained from each individual animal was then compared to the average fluorescent signal and any animal with a 30% or more decrease in fluorescent signal (as compared to the average) is slated for re-imaging. Using the following formula, the % change in Fluorescence signal for each mouse was determined:

$$FLI \text{ Normalization Factor } (\%) = (FLI \text{ signal} - \text{average } FLI \text{ signal})/\text{average } FLI \text{ signal} \quad \text{Equation (1):}$$

Figure 4:
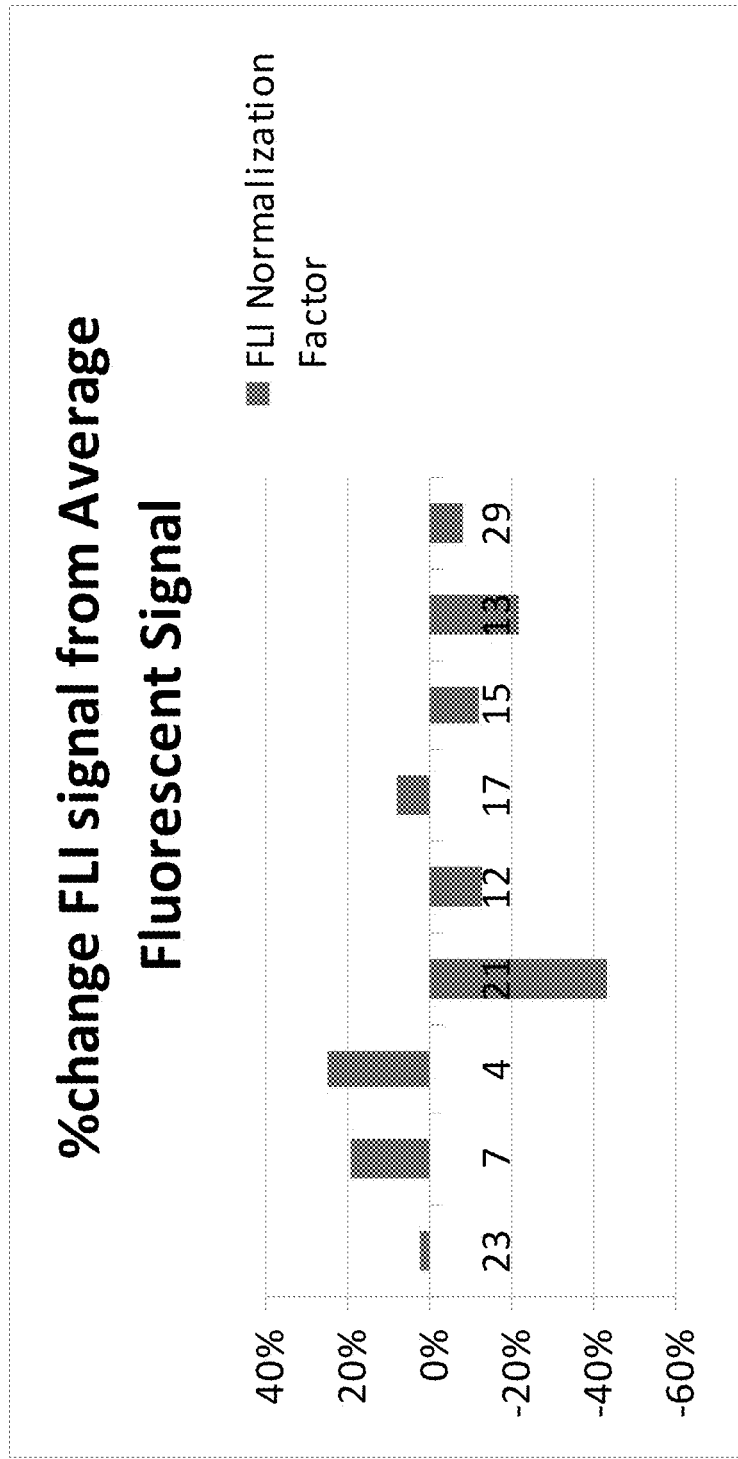
FIG. 4 is a graph showing the percent change from the average fluorescence (FLI) signal in the indicated individual animal.

Fluorescence signal normalization results as obtained using Equation (1) are shown in Table 2 and FIG. 4.

TABLE 2

|    | FLI Normalization Factor (%) |
|----|------------------------------|
| 23 | 2%                           |
| 7  | 19%                          |
| 4  | 25%                          |
| 21 | −43%                         |
| 12 | −13%                         |
| 17 | 8%                           |
| 15 | −12%                         |

TABLE 2-continued

| | FLI Normalization Factor (%) |
|---|---|
| 13 | −21% |
| 29 | −8% |

Since mouse 21 showed a decrease (−) of 43% change in fluorescent signal as compared to the average Fluorescent signal, this animal would be re-imaged.

For animals that do not need to be re-imaged, the fluorescence (FLI) Normalization Factor can be used to normalize the bioluminescent (BLI) signal, using the following equations:

$$BLI\text{ Normalization Value} = BLI \times FLI\text{ Normalization Factor} \quad \text{Equation (2)}$$

$$\text{Normalization } BLI = BLI - BLI\text{ Normalization Value} \quad \text{Equation (3)}$$

Figure 5:
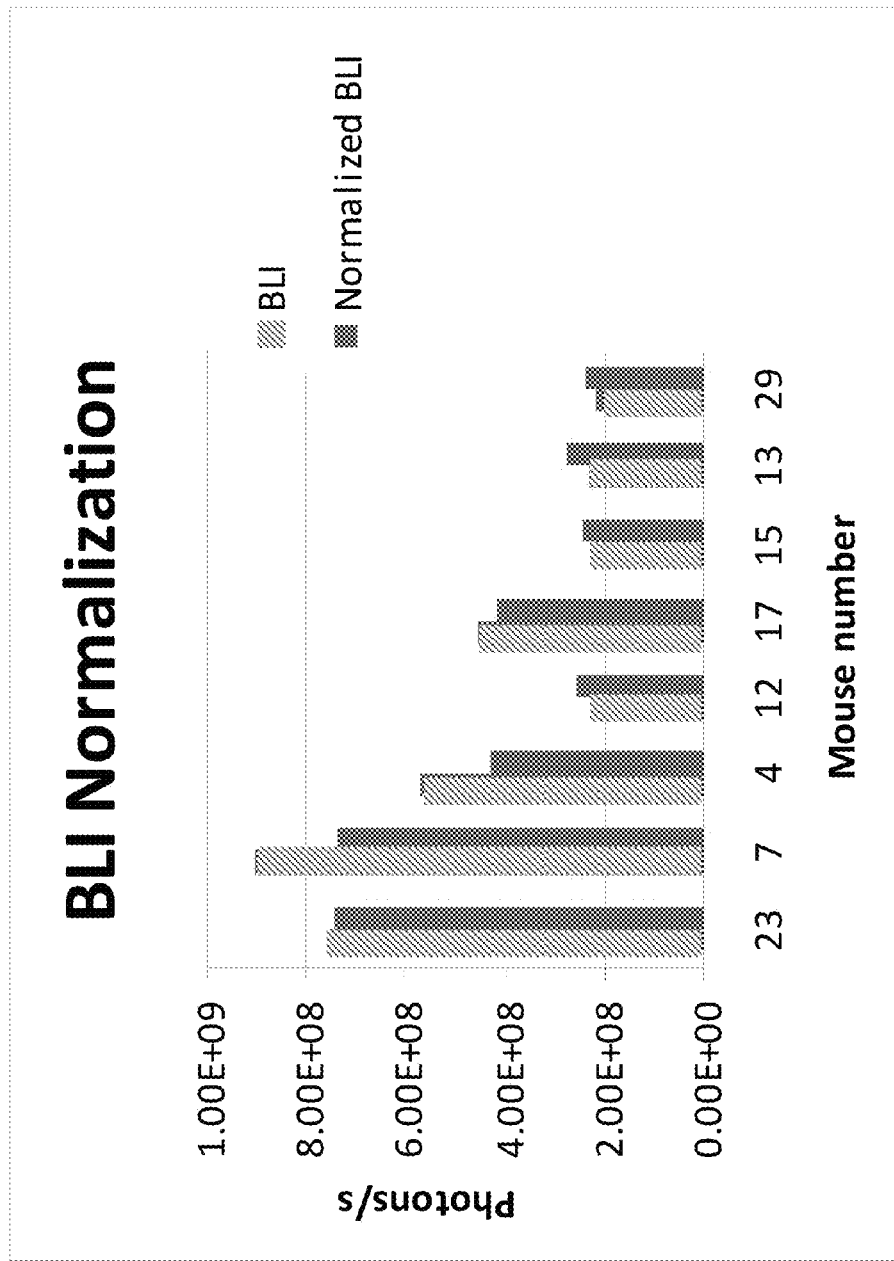
FIG. 5 is a graph showing bioluminescent (BLI), normalized using the fluorescence (FLI) signal.

For animals in which the percent change of the fluorescent signal is below 0% (e.g., mice #12, 15, 13 and 29), the fluorescence normalization value is applied to the quantified Bioluminescent signal. Likewise, if the percent change of fluorescent signal is above 0% (e.g., mice #23, 7, 4, 12, and 17), the normalized value is subtracted from the quantified Bioluminescent signal. Results of the calculations are shown in Table 4 and FIG. 5.

TABLE 4

| | BLI | FLI Normalization Factor (%) | BLI Normalization Value | Normalized BLI |
|---|---|---|---|---|
| 23 | 7.56E+08 | 2% | 1.51E+07 | 7.41E+08 |
| 7 | 9.07E+08 | 19% | 1.72E+08 | 7.35E+08 |
| 4 | 5.73E+08 | 25% | 1.43E+08 | 4.30E+08 |
| 12 | 2.24E+08 | −13% | −2.91E+07 | 2.53E+08 |
| 17 | 4.53E+08 | 8% | 3.62E+07 | 4.17E+08 |
| 15 | 2.19E+08 | −12% | −2.63E+07 | 2.45E+08 |
| 13 | 2.28E+08 | −21% | −4.80E+07 | 2.76E+08 |
| 29 | 2.20E+08 | −8% | −1.76E+07 | 2.38E+08 |

Thus, compositions and methods as described herein can be used to normalize and therefore statistically validate bioluminescence measurements in living animals. Although preferred embodiments have been described in some detail, it is understood that obvious variations can be made without departing from the spirit and the scope of the disclosure.

What is claimed is:

1. A live non-human mammalian animal comprising: (i) an exogenous transgene encoding a bioluminescent protein; and (ii) a composition comprising a bioluminescent substrate and a fluorescent tracking dye, wherein the bioluminescent substrate and the fluorescent tracking dye emit light of different wavelengths and further wherein the bioluminescent substrate is transformed to an excited state in the presence of an oxygenase, oxygen, and ATP, and wherein the fluorescent tracking dye is not a protein.

2. The live animal of claim 1, wherein the bioluminescent substrate comprises luciferin.

3. The live animal of claim 1, wherein the composition further comprises a buffer.

4. The live animal of claim 1, wherein the tracking dye emits green light.

5. The live animal of claim 1, wherein the tracking dye emits red light.

6. The live animal of claim 1, wherein the tracking dye emits purple light.

7. The live animal of claim 1, wherein the tracking dye emits violet light.

8. The live animal of claim 1, wherein the tracking dye emits blue light.

9. The live animal of claim 1, wherein the tracking dye emits yellow light.

10. The live animal of claim 1, wherein the tracking dye emits orange light.

11. The live animal of claim 1, wherein the tracking dye emits near infra-red (IR) light.

* * * * *